United States Patent
Godek et al.

(10) Patent No.: US 9,284,291 B2
(45) Date of Patent: Mar. 15, 2016

(54) KAPPA OPIOID RECEPTOR COMPOUNDS

(71) Applicants: Dennis Michael Godek, Glastonbury, CT (US); Harry Ralph Howard, Bristol, CT (US)

(72) Inventors: Dennis Michael Godek, Glastonbury, CT (US); Harry Ralph Howard, Bristol, CT (US)

(73) Assignee: MediSynergies, LLC, Newington, CT (US)

( * ) Notice: Subject to any disclaimer, the term of this patent is extended or adjusted under 35 U.S.C. 154(b) by 0 days.

(21) Appl. No.: 14/445,851

(22) Filed: Jul. 29, 2014

(65) Prior Publication Data

US 2016/0031844 A1 Feb. 4, 2016

(51) Int. Cl.
*C07D 307/87* (2006.01)
*A61K 31/343* (2006.01)
*A61P 25/18* (2006.01)
*A61P 25/22* (2006.01)
*A61P 25/24* (2006.01)
*A61P 25/30* (2006.01)
*C07D 413/06* (2006.01)
*C07D 405/06* (2006.01)
*C07D 405/04* (2006.01)

(52) U.S. Cl.
CPC ............ *C07D 307/87* (2013.01); *A61K 31/343* (2013.01); *C07D 405/04* (2013.01); *C07D 405/06* (2013.01); *C07D 413/06* (2013.01)

(58) Field of Classification Search
CPC .. C07D 307/78; C07D 307/81; C07D 307/82; C07D 307/87; A61K 31/343
USPC ......................................... 549/355; 514/469
See application file for complete search history.

(56) References Cited

U.S. PATENT DOCUMENTS

| 6,365,747 B1 * | 4/2002 | Dall'Asta | C07D 263/14 548/146 |
| 2015/0038507 A1 * | 2/2015 | Godek | C07D 405/04 514/233.5 |

* cited by examiner

*Primary Examiner* — Venkataraman Balasubramanian

(57) ABSTRACT

The invention is directed to a compound of formula I, as defined herein, or a pharmaceutically acceptable salt thereof; a pharmaceutical composition containing a compound of formula I, a method of treatment of a disorder or condition that may be treated by administration of the compound, the method comprising administering to a mammal in need of such treatment a compound of formula I as described above, and a method of treatment of a disorder or condition selected from the group consisting of depression, mood disorders, schizophrenia, Alzheimer's disease, anxiety and addiction, the method comprising administering to a mammal, including a human, in need of such treatment a compound of formula I as described above.

12 Claims, No Drawings

KAPPA OPIOID RECEPTOR COMPOUNDS

This application claims the priority benefits from U.S. Provisional Application No. 61/697,799 filed Sep. 6, 2012 and U.S. Provisional Application No. 61/862,964 filed Aug. 7, 2013.

BACKGROUND OF THE INVENTION

This invention is directed to compounds of the formula I described herein, to a pharmaceutical composition comprising such compounds and to methods of preventing or treating disorders or conditions that may be treated by administration of such compounds to a mammal in need, including humans. In particular, the compounds of the current invention are potentially useful for treating, e.g., depression, mood disorders, schizophrenia, Alzheimer's disease and addiction.

Depression is a disease that afflicts a large segment of the U.S. population, estimated to be more than 20 million patients (Kessler, R. C., et al, *Archives of General Psychiatry*, 2005, 62 (6):617-27). Symptoms of depression include alteration in mood (e.g., sadness, apathy), negative self-concept (e.g., self-reproach), vegetative changes (e.g., insomnia, anorexia, loss of libido), and changes in activity level (e.g., agitation, listlessness); it may be uni-polar or bi-polar (i.e., manic-depression). Traditionally, treatment of depressed individuals has included the use of psychotherapy, natural and/or synthetic pharmacological agents, or a combination of the two. Natural agents include substances such as St. John's Wort.

Since the 1950's, pharmacological substances have played a dominant role in the treatment and recovery of patients. Following the recognition of the role of the neurotransmitter (NT) serotonin (5-hydroxytryptamine, 5-HT) in the Central Nervous System (CNS), more effective drugs have been designed and marketed to regulate this mood disorder. The drugs that are currently available—and most often prescribed—for the treatment of depression include serotonin selective reuptake inhibitors (SSRI's, e.g., fluoxetine, sertraline), serotonin-norepinephrine reuptake inhibitors (SNRI's, e.g., venlafaxine, duloxetine), tricyclic antidepressants (TCA's, e.g., desipramine, nortriptyline, amitriptyline) which influence norepinephrine levels, and other NTs in the CNS. While many of these therapeutic agents provide benefit to the patients who take them as prescribed, it may take several weeks or longer to achieve significant clinical relief from their most serious symptoms—a major concern for physicians dealing with patients at risk of suicide. Furthermore, it is estimated that approximately 30% or more of diagnosed patients do not achieve adequate clinical relief even after treatment with three or more different antidepressant medications. Coupled with potential side effects (e.g., gastrointestinal disturbances, sexual dysfunction and reduced libido) as well as development of potentially life-threatening serotonin syndrome, physicians and their patients are eagerly awaiting discovery of safer and more broadly efficacious treatments.

There continues to be great interest in identifying novel mechanisms of action for the treatment of depression and related mood disorders. Recently, interest has been drawn to the use of selective opioid agonists and antagonists, specifically those that interact with the kappa (κ) subtype, as a means of achieving faster onset of action with potentially better toleration (Carlezon, W. A., et al, *Pharmacology & Therapeutics*, 2009), (Zhang, H., et al, *European Journal of Pharmacology*, 2007, 570:89-96), (Todtenkopf, M. S., et al, *Psychopharmacology (Berl.)* 2004, Jan. 16), (Ibegbu, A. O., et al, *British Journal of Pharmacology and Toxicology*, 2011, 2(2): 84-91) and (Gharagozlou, P., et al, *BioMed Central Pharmacology (Open Access)*, 2006, Jan. 25). Mague, et al (*Journal of Pharmacology and Experimental Therapeutics*, 2003, 305: 323-330) have published results of activity in a rat forced-swim test that demonstrate the potential for antidepressant activity of kappa opioid receptor (KOR) antagonists.

A review of the role of opioid receptors in the development of mood disorders is also available (Lutz, P.-E. and Kieffer, B. L., *Trends in Neurosciences*, 2013, 36(3):195-206). A. T. Knoll and W. A. Carlezon (*Brain Research*, 2010, 1314:56-73) have also reported the results of their studies of the roles of dynorphin and KOR with respect to the role of stress in depression.

M. Bartolato, et al (*Biological Psychiatry*, 2005, 57:1550-1558) have claimed positive results from studies of KOR agonists in a rat model of schizophrenia—disruption of prepulse inhibition—which suggest a possible therapeutic benefit for compounds having this activity. S. Yoshikawa, et al (*European Journal of Pharmacology*, 2009, 606:102-108) have also described their findings with the KOR agonist TRK-820 in rat models of schizophrenia and suggest a therapeutic potential for this compound in the treatment of psychotic behavior.

Kappa receptors have further been implicated in addictive behavior and antagonists have shown potential utility in a mouse model of nicotine addiction and withdrawal (Jackson, K. J., et al, *Psychopharmacol.*, DOI 10.1007/s00213-010-1803-1).

B. Hahn, et al, (*Neuropharmacology*, 2000, 39:2848-2855) have studied modulation of nicotine-induced behavior with Kappa agonists in rats. J. L Kissler, et al (*Biological Psychiatry*, 2013) have studied the potential utility of KOR substances in alcohol self-administration, whereas the value of KOR selective compounds for the treatment of opioid and stimulant addiction was reviewed by S. D. Glick, et al (*Brain Research*, 1995, 681:147-152) and E. R. Butelman, et al (*Trends in Neurosciences*, 2012, 35(10):587-596).

Kappa opioid receptors, interacting with the dynorphin system in the CNS, also appear to play a significant role in other psychiatric disorders, including anxiety (e.g., see Tejeda, H. A., et al, *Cellular and Molecular Life Science*, 2011, 69:857-896; Peters, M. F., et al, *European Journal of Pharmacology*, 2011, 661:27-34) and therefore KOR agonists or antagonists may offer a therapeutic value in treating anxiety disorders.

Kappa opioid receptors also appear to play a role in neuroinflammatory diseases, such as Alzheimer's disease and Huntington's disease (see Park S W, Wie L N, 2014, "Can GPCR such as Kappa Opioid Receptor, be a Viable Therapeutic Target for Reducing or Preventing Neuroinflammation?", *Clinical and Experimental Pharmacology*, 4:e127. Doi: 10.4172/2161-1459.1000e127). Thus, drugs which selectively interact with KOR receptors may offer newer treatment options for patients suffering from these debilitating diseases.

KOR antagonists have been disclosed, e.g., in U.S. Pat. No. 6,534,514 (Portoghese, P. S., et al, Issued Mar. 18, 2003), U.S. Pat. No. 6,559,159 (Carroll, F. I., et al, Issued May 6, 2003) and U.S. Pat. No. 7,709,522 (Buezo, N. D., et al, Issued May 4, 2010). Similarly, kappa agonists have been disclosed in U.S. Pat. No. 5,804,595 (Portoghese, P. S., et al, Issued Sep. 8, 1998) and U.S. Pat. No. 6,191,126 (Gamache, D. A.; Issued Feb. 20, 2001). The syntheses and receptor selectivity of novel chemotypes which exhibit potent antagonist or agonist activity at the KOR have also been described by K. J. Frankowski, et al (*ACS Chemical Neuroscience*, 2012, 3:221-236), C. H. Mitch, et al (*Journal of Medicinal Chemistry*, 2011, 54:8000-8012), T. E. Prisinzano, (*Journal of Medicinal*

*Chemistry,* 2013, 56:3435-3443) and C. M. Kormos, et al, (*Journal of Medicinal Chemistry,* 2013, 56:4551-4567). T. A. Brugel, et al (*Bioorganic and Medicinal Chemistry Letters,* 2010, 20:5405-5410 and 20:5847-5852) have also disclosed a novel series of azabicyclo[3.2.1]octan-3-yloxy-benzamides with potent and selective K antagonist activity.

It has recently been reported that the biotech company Alkermes has initiated a Phase 2 study of ALKS 5461, a combination of buprenorphine (a mixed kappa opioid receptor antagonist/mu opioid receptor agonist which has demonstrated antidepressant properties in human studies) and ALKS 33 (i.e., samidorphan), a selective mu opioid receptor antagonist that does not affect the delta- or kappa-opioid receptors) in clinical trials of patients suffering from major depressive disorder (http://en.wikipedia.org/w/index.php?title=Samidorphan&oldid=555540304).

This U.S. patent application claims benefit of U.S. provisional patent application Ser. No. 61/697,799, filed Sep. 6, 2012, which provisional application is incorporated herein by specific reference in its entirety.

SUMMARY OF THE INVENTION

This invention is directed to compounds of the formula I:

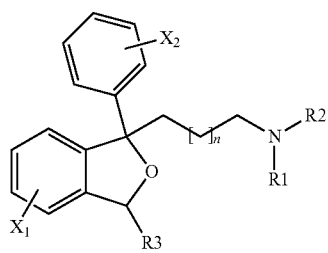

(I)

or the pharmaceutically acceptable salt(s) thereof, wherein:
$X_1$ is a group of the general formula:

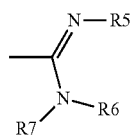

(II)

wherein R5, R6 and R7 are independently defined as H, $C_1$-$C_6$ alkyl, $C_3$-$C_7$-cycloalkyl, -(un)substituted aryl, or heteroaryl; or $X_1$ is a heteroaryl ring, including, for example, 2-imidazolyl, 4-imidazolyl, 2-thiazolyl, 4-thiazolyl, 5-thiazolyl, 2-oxazolyl, 4-oxazolyl, 5-oxazolyl, 1,2,4-thiadiazol-3-yl, 1,2,4-thiadiazol-2-yl, 1,2,4-thiadiazol-4-yl, 1,2,3-triazolyl-2-yl, 1,2,3-triazol-1-yl, 1,2,4-triazol-1-yl, 1,2,4-triazol-3-yl, 1,2,4-triazol-4-yl, 1,3-thiazol-2-yl, 1,3-thiazol-4-yl, 1,2,3,4-tetrazol-5-yl, 1,2,3,4-tetrazol-1-yl, 1,2,4-oxadiazol-3-yl, 1,2,4-oxadiazol-2-yl, 1,2,4-oxadiazol-3-yl, 1,2,4-oxadiazol-5-yl, 1,3-pyrimidin-2-yl, 1,2-pyrazin-3-yl, 1,2,4-triazin-3-yl;

R5 and R6, taken together with the N—C=N group to which they are attached form a 5- to 10-member cyclic or bicyclic ring, optionally substituted with up to two additional heteroatoms selected from the group consisting of N, O or S (including, for example, the cyclic or bicyclic rings imidazole, oxadiazole, thiadiazole, benzimidazole) and optionally substituted with H, $C_1$-$C_6$ alkyl or cycloalkyl groups, (un)substituted aryl or heteroaryl rings, or oxygen, e.g., sulfoxide or sulfone); or R6 and R7, taken together with the nitrogen atom to which they are attached form a 5- to 10-member cyclic or bicyclic ring, optionally substituted with up to two additional heteroatoms selected from the group consisting of N, O or S (including, for example, the cyclic or bicyclic rings azetidine, pyrrolidine, piperidine, azepine, piperazine, morpholine, thiomorpholine) and optionally substituted with H, $C_1$-$C_6$ alkyl or cycloalkyl groups, aryl or heteroaryl rings, or oxygen, e.g., sulfoxide or sulfone);

$X_2$ is H, Cl, or F;

R1 and R2 are independently hydrogen or methyl;

R3 is hydrogen; and n is zero, one or two.

The invention is also directed to a pharmaceutical composition for treating, for example, a disorder or condition (e.g., depression, mood disorders, schizophrenia, Alzheimer's disease, addiction, anxiety) in a mammal, including a human, that may be treated by administering to said mammal in need of such treatment a compound of formula I as described above, or a pharmaceutically acceptable salt thereof, that is effective in treating such disorder or condition, and a pharmaceutically acceptable carrier.

The invention is also directed to a method of treatment of a disorder or condition selected from the group consisting of the disorders or conditions listed in the preceding paragraph (e.g. depression, mood disorders, schizophrenia, anxiety, Alzheimer's disease, addiction), the method comprising administering to said mammal in need of such treatment an amount of a compound of formula I as described above that is effective in treating such disorder or condition.

The invention also relates to the use of a compound of the formula I, or a pharmaceutically acceptable salt thereof, in the manufacture of a medicament for the treatment of a disorder or condition, as listed in the preceding paragraph, the treatment of which can be effected or facilitated by administration of an effective amount of the medicament to a mammal, including a human, in need of such treatment.

Preferred embodiments of the present invention include the compounds of formula I in which:

(A) R1 and R2 are independently methyl;

$X_1$ is C(=NR5)-NR6R7 (formula II); and n is one.

(B) R1 and R2 are independently methyl;

$X_1$ is a heteroaryl ring as previously defined; and n is one.

The most preferred embodiment of the present invention includes the compounds of formula I in which $X_1$ is a group of the formula R1 and R2 are each methyl;

R3 is hydrogen;

$X_1$ is a heteroaryl ring as previously defined;

$X_2$ is 4-fluoro; and n is one.

Preferred compounds of formula I in accordance with the present invention include the following:

2-(1-[3-(methylamino)propyl]-1-(4-fluorophenyl)-1,3-dihydro-2-benzofuran-5-yl])-1H-imidazole;

Other preferred compounds of the general formula include the following:

2-(1-[3-(dimethylamino)propyl]-1-(4-fluorophenyl)-1,3-dihydro-2-benzofuran-5-yl])-1,3-thiazole;

2-(1-[3-(dimethylamino)propyl]-1-(4-fluorophenyl)-1,3-dihydro-2-benzofuran-5-yl])-1,3-oxazole;

4-(1-[3-(dimethylamino)propyl]-1-(4-fluorophenyl)-1,3-dihydro-2-benzofuran-5-yl])-1,3-thiazole;

2-(1-[3-(dimethylamino)propyl]-1-(4-fluorophenyl)-1,3-dihydro-2-benzofuran-5-yl])-1,3-thiazole;

3-(1-[3-dimethylamino)propyl]-1-(4-fluorophenyl)-1,3-dihydro-2-benzofuran-5-yl])-1,2-isothiazole;

4-(1-[3-(dimethylamino)propyl]-1-(4-fluorophenyl)-1,3-dihydro-2-benzofuran-5-yl])-2-methyl-1H-imidazole;

5-(1-[3-(dimethylamino)propyl]-1-(4-fluorophenyl)-1,3-dihydro-2-benzofuran-5-yl])-2,4-dimethyl-1H-imidazole;

2-(1-[3-(dimethylamino)propyl]-1-(4-fluorophenyl)-1,3-dihydro-2-benzofuran-5-yl])-1H-1,3,4-triazole;

2-(1-[3-(dimethylamino)ethyl]-1-(4-fluorophenyl)-1,3-dihydro-2-benzofuran-5-yl])-1 H-imidazole;

2-(1-[3-(dimethylamino)butyl]-1-(4-fluorophenyl)-1,3-dihydro-2-benzofuran-5-yl])-1H-imidazole;

2-(1-[3-(dimethylamino)propyl]-1-(4-fluorophenyl)-1,3-dihydro-2-benzofuran-5-yl])-4-methyl-1H-imidazole;

5-(1-[3-(dimethylamino)propyl]-1-(4-fluorophenyl)-1,3-dihydro-2-benzofuran-5-yl])-1H-tetrazole;

1-(1-[3-(dimethylamino)propyl]-1-(4-fluorophenyl)-1,3-dihydro-2-benzofuran-5-yl])-5-methyl-2H-tetrazole;

3-(1-[3-(dimethylamino)propyl]-1-(4-fluorophenyl)-1,3-dihydro-2-benzofuran-5-yl])-1,2,4-thiadiazole;

3-(1-[3-(dimethylamino)propyl]-1-(4-fluorophenyl)-1,3-dihydro-2-benzofuran-5-yl])-1,2,4-oxadiazole;

1-methyl-2-(1-[3-(dimethylamino)propyl]-1-(4-fluorophenyl)-1,3-dihydro-2-benzofuran-5-yl])-1H-imidazole.

4-methyl-2-(1-[3-(dimethylamino)propyl]-1-(4-fluorophenyl)-1,3-dihydro-2-benzofuran-5-yl])-1H-imidazole.

2(S)-2-(1-[3-(dimethylamino)propyl]-1-(4-fluorophenyl)-1,3-dihydro-2-benzofuran-5-yl])-1H-imidazole.

2(R)-2-(1-[3-(dimethylamino)propyl]-1-(4-fluorophenyl)-1,3-dihydro-2-benzofuran-5-yl])-1H-imidazole.

2-(1-[3-(dimethylamino)propyl]-1-(4-fluorophenyl)-1,3-dihydro-2-benzofuran-5-yl])-1H-benzimidazole;

4,5-dimethyl-2-(1-[3-(dimethylamino)propyl]-1-(4-fluorophenyl)-1,3-dihydro-2-benzofuran-5-yl])-1H-imidazole;

2-[1-[3-(dimethylamino)propyl]-1-(4-fluorophenyl)-1,3-dihydro-2-benzofuran-5-yl]-1,2,3,4-tetrahydro-1H-isoquinolin-2-yl)methanimine;

2-(1-[3-dimethylaminopropyl]-1-(4-fluorophenyl)-1,3-dihydro-2-benzofuran-5-yl})-1,3-pyrimidine;

3-(1-[3-dimethylaminopropyl]-1-(4-fluorophenyl)-1,3-dihydro-2-benzofuran-5-yl})-1,2,4-triazine;

2-(1-[3-(dimethylamino)propyl]-1-(4-fluorophenyl)-1,3-dihydro-2-benzofuran-5-yl)-1 H-4,5-dihydro-imidazole;

2-(1-[3-(dimethylamino)propyl]-1-(4-fluorophenyl)-1,3-dihydro-2-benzofuran-5-yl)-4,5,6,7-tetrahydro-1H-1,3-diazepine; and 2-(1-[3-(dimethylamino)propyl]-1-(4-fluorophenyl)-1,3-dihydro-2-benzofuran-5-yl)-1,4,5,6-tetrahydro-pyrimidine.

The most preferred compounds of the invention include:

2-(1-[3-(dimethylamino)propyl]-1-(4-fluorophenyl)-1,3-dihydro-2-benzofuran-5-yl])-1H-imidazole;

A preferred use for compounds of formula I is in the treatment of depression, mood disorders, schizophrenia, Alzheimer's disease, anxiety and addiction. More specifically, the compounds of formula I are useful in the treatment of a variety of mood disorders including single and/or recurrent major depressive disorder, dysthymic disorder and depressive disorder not otherwise specified (NOS), as well as bipolar disorders, e.g., bipolar I disorder, bipolar II disorder, cyclothymic disorder and mood disorders not otherwise specified (NOS), as defined in the Diagnostic and Statistical Manual of Mental Disorders, 4$^{th}$ Edition (DSM-IV) published by the American Psychiatric Association, June 2000.

DETAILED DESCRIPTION OF THE INVENTION

The compounds of formula I may be prepared as described in the following reaction schemes and discussions. Unless otherwise indicated, $X_1$, $X_2$, R1, R2, R3, R4, R5, R6, R7, R8 and R9, and structural formulae II, III, IV, VI, VIIa, VIIb, VIII, IX in the reaction schemes and discussion that follow are as defined above.

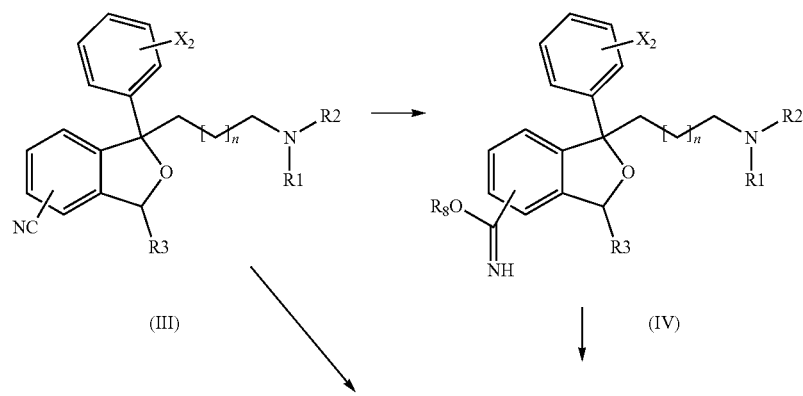

Scheme 1

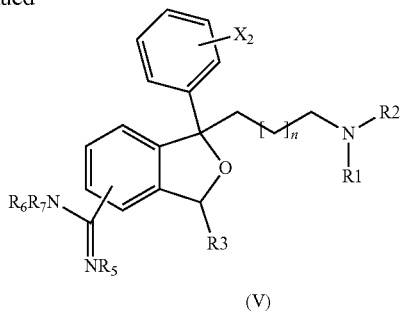

(V)

According to Scheme 1, compounds of the general formula III may be converted to an imino-ether (i.e., imidate) of the general formula IV, and next converted to an amidine of the general formula V using the appropriate primary or secondary amine HNR6R7. One efficient method for this process is via the Pinner reaction, which involves treatment of the nitrile of formula III with an anhydrous acid, preferably hydrochloric acid, and a low molecular weight alcohol $R_8OH$ such as methanol or ethanol, preferably ethanol, at a temperature in the range from about 0° C. to about the boiling point of the alcohol used, preferably at about 80° C. for ethanol, and at a pressure of about one to three atmospheres, preferably at atmospheric pressure, to generate the intermediate imino-ether IV. The crude intermediate IV can then be reacted with an appropriate amine of the general formula HNR6R7 present in a ratio of 0.5 to 5 equivalents, preferably in a ratio of 1 to 3 equivalents, to produce the amidine compounds of general formula V (i.e., general formula I where $X_1$ is —C(=NR5)-NR6R7, i.e., formula II). This process is described in a number of organic syntheses texts, including Jie Jack Li, *Name Reactions: A Collection of Detailed Mechanisms and Synthetic Applications* (4th Ed.), pp. 438-9, Springer-Verlag, N.Y., 2009). Additional examples of the Pinner reaction and modifications can be found in Saul Patai, *The Chemistry of Amidines and Imidates*, Wiley, N.Y., 1975, pp. 385-489. Another useful review is by R. Roger and D. Neilson, *Chemical Reviews*, 1961, 61(2), 179-211.

The starting materials for this process, compounds of the general formula III, are available using procedures described in the chemical and patent literature. For example, the compound of formula III, wherein n=1, R1=CH3, R2=CH3, R3=H, $X_2$ is 4-fluoro and the CN group is attached to the 5-position of the benzofuran ring has been commercially available as the antidepressant citalopram (in racemic form) and as the antidepressant escitalopram (as the single, (S)-isomer). Procedures for the syntheses of these compounds are also readily available in the literature (e.g., see M. Pitts, *Tetrahedron*, 2006, 62, 4705-4708; N. Periyandi, et al, PCT Int. Appl., (2006), WO-2006021971; T. Ikemoto and Y. Watanabe, PCT Int. Appl., (2005), WO-2005082842; H. Ahmadian and H. Petersen, PCT Int. Appl., (2003), WO-2003051861; H. Petersen, PCT Int. Appl. (2001), WO-2001068631; L. Dall'Asta, et al, PCT Int. Appl., (2000), WO-2000023431).

Alternatively, the imino-ether of general formula IV may be isolated, e.g. as a hydrochloride salt, which may be converted to the free imino-ether by treatment with a weak base such as sodium bicarbonate, or purified and subsequently reacted with the appropriate amine of general formula HNR6R7 to generate the desired product of general formula V.

In some cases, it may also be desirable to convert the nitrile group of the compound of formula II directly into the amidine group present in the compound of formula V (i.e., compound of formula I wherein $X_1$ is —C(=NR5)-NR6R7). Examples of this process are found in G. Rousselet, et al, *Tetrahedron Letters*, 1993, 34(40), 6395-6398, and R. Garigipati, *Tetrahedron Letters*, 1990, 31(4), 1969-1972.

According to Scheme 2, a compound of the general formula III, may be converted directly into an amidine of general formula V using an excess of ammonia under conditions normally employed in the Pinner reaction (see above). These simple amidines of general formula VI can then be converted to the desired compounds of general formula V (i.e., general formula I wherein $X_1$ is a heterocyclic ring, including imidazole). Procedures for this conversion may be found in the chemical literature and are familiar to one skilled in the art of organic synthesis. For example, conversion of intermediate VI, wherein R1 and R2 are methyl, R3 is hydrogen, n equals 1 and $X_2$ is 4-fluoro, to a compound of general formula V can be accomplished using an amino-acetal, followed by ring closure to produce the heterocyclic imidazole ring (e.g., see R. Frutos, et al, *Tetrahedron Letters*, 2005, 46(48), 8369-8372). Other heterocyclic ring systems that can be prepared in this manner include, for example, benzimidazolyl and 1,3-pyrimidinyl.

Scheme 2

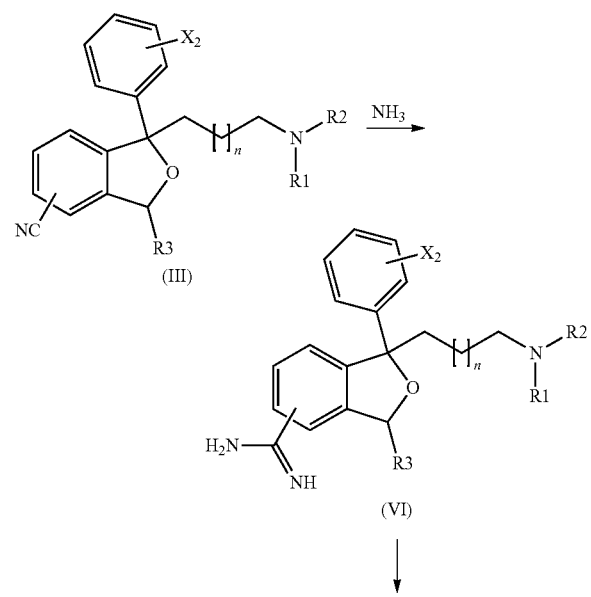

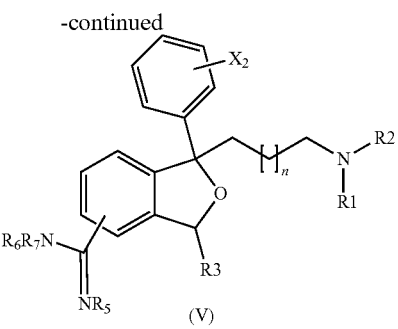

In another embodiment, the nitrile compound of formula III can be reacted with e.g., sodium azide to directly generate a tetrazole derivative of general formula I, wherein $X_1$ is:

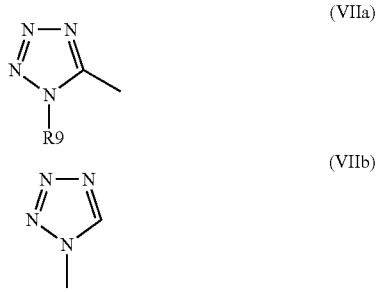

and R9 is H or $C_1$-$C_3$ alkyl (see, for example, B. Das, et al, *Synlett,* 2010, 391-394; J. Roh, et al, *Synthesis,* 2009, 2175-2178; D. Cantillo, et al, *Journal of the American Chemical Society,* 2011, 133, 4465-4475; W.-K. Su, *European Journal of Organic Chemistry,* 2006, 2723-2726.

Scheme 3

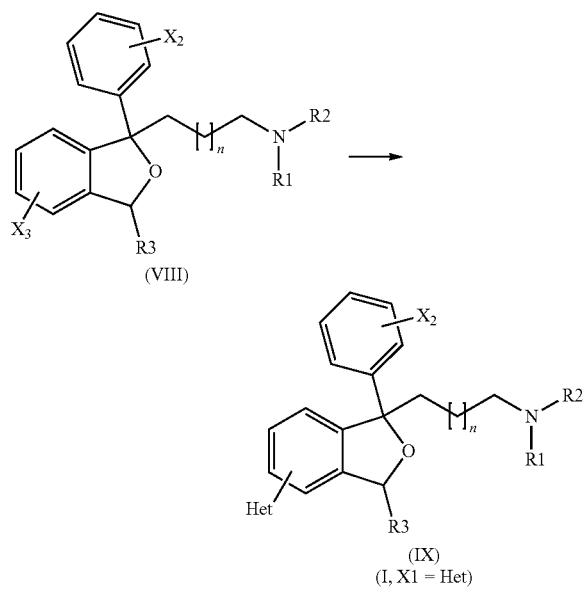

In another embodiment, an intermediate of the general formula VIII, wherein X3 is as defined below, can be converted into a compound of the general formula IX (i.e., general formula I, wherein $X_1$ is a heteroaryl group, using one or more of a variety of methods described in the chemical literature. This can be accomplished via a process referred to as a Suzuki (or Suzuki-Miyaura) coupling reaction (e.g., see K. Wong, et al, *Journal of Organic Chemistry,* 2002, 67(3), 1041-1044). The reaction typically employs a palladium catalyst to couple an aryl halide with an aryl, or heteroaryl, boronic acid or boronate ester. Examples of this reaction can be found in, for example, L. Wang, et al, *European Journal of Organic Chemistry,* 2012, (3), 595-603; M. Li, et al, *Tetrahedron Letters,* 2009, 50(13), 1478-1481; J. C. W. Evans, et al, *Organic Synthesis,* 1938, 18. Modifications to this coupling process include the use of other metals, such as magnesium (for the preparation of 1,2,3-triazines—see, A. Ohsawa, et al, *Journal of the Chemical Society, Chemical Communications,* 1985, (20), 1370); cesium and copper (I) (see H. Yang, et al, *Letters in Organic Chemistry,* 2011, 8(5), 325-331; C. Cao, et al, *Synthetic Communications,* 2012, 42(2), 279-284) and microwave conditions (see H. Huang, *Journal of Combinatorial Chemistry,* 2008, 10(5), 617-619). A modification of the Ullmann reaction to prepare substituted 1,2,4-triazoles has also been described (see P. Suresh, et al, *Journal of Organic Chemistry,* 2008, 73(22), 9121-9124).

The starting materials for this process, compounds of the general formula VIII, wherein $X_3$ is, e.g., chlorine, bromine or iodine, are described in the chemical literature, or may be commercially available (e.g., see J. Eildal, et al, *Journal of Medicinal Chemistry,* 2008, 51, 3045). The aryl, or heteroaryl, boronic acids or esters may be obtained from commercial sources (e.g., Sigma-Aldrich Chemical, St. Louis, Mo.), or prepared as described in the chemical literature (e.g., see P. Zhang, et al, *Journal of Medicinal Chemistry,* 2010, 53, 6112-6121; P. Bartlett, et al, *Chemical Reviews,* 1997, 97, 1281; R. Batey, et al, *Journal of the American Chemical Society,* 1999, 121, 5075; J. Bird, et al, *Journal of Medicinal Chemistry,* 1994, 37, 158).

Where cis- and trans-isomers are possible for an embodiment of the inventive compounds of formula I, both cis- and trans-isomers (i.e., diastereomers) are within the scope of this invention. Similarly, when R- and S-, or (+)- and (−)-, or d- and l-isomers (i.e., enantiomers) are possible for an embodiment of the inventive compounds of formula I, each and every one of said isomers are within the scope of this invention.

The term "alkyl" refers to straight or branched chains of carbon atoms. Exemplary alkyl groups are $C_3$-$C_{10}$ alkyl groups which include methyl, ethyl, propyl, isopropyl, butyl, isobutyl, pentyl, isopentyl, hexyl and the like, including all regioisomeric forms thereof, and straight and branched chain forms thereof. The term "alkyl" is also used to denote straight or branched chains of carbon atoms having one or more carbon-carbon double bonds, such as vinyl, allyl, butenyl and the like, as well as straight and branched chains of carbon atoms having one or more carbon-carbon triple bonds, such as ethynyl, propargyl, butynyl, and the like.

The term "aryl" denotes a cyclic, aromatic hydrocarbon. Examples include phenyl, naphthyl, anthracenyl, phenanthracenyl, and the like.

The terms "alkoxy" and "aryloxy" denote "O-alkyl" and "O-aryl", respectively. The term "cycloalkyl" denotes a cyclic group of carbon atoms, where the ring formed by the carbon atoms may be saturated or may comprise one or more carbon double bonds in the ring. Examples of cycloalkyl groups include cyclopropyl, cyclobutyl, cyclopentyl, cyclohexyl, cycloheptyl, and the like as well as cyclopentenyl, cyclopentadienyl, cyclohexenyl, cyclohexadienyl, and the like. As used herein, the term "cycloalkyl" is also intended to denote a cyclic group comprising at least two fused rings, such as adamantyl, decahydronaphthalinyl, norbornanyl, where the cyclic group may also have one or more carbon-carbon double bonds in one or more rings, such as in bicyclo(4.3.0)nona-3,6(1)-dienyl, dicyclopentadienyl, 1,2,3,4-tetrahydronaphthalinyl (tetralinyl), indenyl, and the like.

The term "one or more substituents" as used herein, refers to a number of substituents that equals from one to the maximum number of substituents possible based on the number of available bonding sites.

The terms "halo" and "halogen", as used herein, unless otherwise indicated, include chloro, fluoro, bromo and iodo.

The term "heteroaryl" denotes a monocyclic or bicyclic aromatic group wherein one or more carbon atoms are replaced with heteroatoms selected from the group consisting of nitrogen, oxygen, and sulfur. If the heteroaryl group contains more than one heteroatom, the heteroatoms may be the same or different. Preferred heteroaryl groups are five- to fourteen-member rings that contain from one to four heteroatoms independently selected from oxygen, nitrogen, and sulfur. Examples of preferred heteroaryl groups include benzo[b]thienyl, chromenyl, furyl, imidazolyl, indazolyl, indolizinyl, indolyl, isobenzofuranyl, isoindolyl, isoquinolinyl, isothiazolyl, isoxazolyl, napthylidinyl, oxadiazolyl, oxazinyl, oxazolyl, phthalazinyl, pteridinyl, purinyl, pyranyl, pyrazinyl, pyrazolyl, pyridazinyl, pyridinyl, The term "treating", as used herein, refers to reversing, alleviating, inhibiting the progress of, or preventing the disorder or condition to which such term applies, or preventing one or more symptoms of such disorder or condition. The term "treatment", as used herein, refers to the act of treating, as "treating" is defined immediately above.

The compounds of formula I of the present invention may also contain functional groups or heterocyclic ring systems that may exist in one or more tautomeric forms. The present invention includes within its scope all such tautomeric forms, including mixtures of such forms.

The compounds of the present invention may have optical centers and therefore may occur in different enantiomeric configurations. Formula I, as depicted above, includes all enantiomers, diastereomers, and other stereoisomers of the compounds depicted in structural formula I, as well as racemic and other mixtures thereof. Individual isomers can be obtained by known methods, such as optical resolution, optically selective reaction, or chromatographic separation in the preparation of the final product or any of its intermediates.

The compounds of formula I may also exist in the form of cis- or trans-isomers with respect to configuration on the furan ring of formula I. Such cis- and trans-isomers are also considered to be within the scope of the present invention, The present invention also includes isotopically labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, sulfur, phosphorus, fluorine, and chlorine, such as $^2$H, $^3$H, $^{11}$C, $^{13}$C, $^{14}$C, $^{13}$N, $^{15}$N, $^{17}$O, $^{18}$O, $^{35}$S, $^{31}$P, $^{32}$P, $^{31}$P, $^{18}$F and, $^{37}$Cl, respectively. Certain isotopically labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with isotopes such as deuterium, i.e., $^2$H, can afford certain therapeutic advantages resulting from greater metabolic stability, for example increased in vivo half-life or reduced dosage requirements and hence may be preferred in some circumstances. Isotopically labeled compounds of formula I of this invention and prodrugs thereof can generally be prepared by carrying out the procedures disclosed in the Schemes and/or the examples and Preparations below, by substituting a readily available isotopically labeled reagent for a non-isotopically labeled reagent.

Compounds of the present invention, prodrugs thereof, and pharmaceutically acceptable salts of said compounds, or of said prodrugs which contain the aforementioned isotopes and/or other isotopes of other atoms are within the scope of this invention.

A "unit dosage form" as used herein is any form that contains a unit dose of the compound of formula I. A unit dosage form may be, for example, in the form of a tablet or a capsule. The unit dosage form may also be in liquid form, such as a solution or suspension.

The compositions of the present invention may be formulated in a conventional manner using one or more pharmaceutically acceptable carriers. Thus, the active compounds of the present invention may be formulated for oral, buccal, intranasal, parenteral (e.g., intravenous, intramuscular or subcutaneous) or rectal administration or in a form suitable for administration by inhalation or insufflations.

For oral administration, the pharmaceutical compositions may take the form of, for example, tablets or capsules prepared by conventional means with pharmaceutically acceptable excipients such as binding agents (e.g., pre-gelatinized maize starch, polyvinylpyrrolidone or hydroxypropyl methylcellulose), fillers (e.g., lactose, microcrystalline cellulose or calcium phosphate); lubricants (e.g., magnesium stearate, talc, or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispensing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrachloroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insulator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., depression) is from about 0.1 mg/kg to about 100 mg/kg of the active ingredient per unit dose which could be administered, for example, one to four times per day. Toxicity concerns at the higher level may restrict intravenous (i.v.) dosages to a lower level, such as up to about 10 mg/kg. A dose of about 0.1 mg/kg to about 100 mg/kg may be employed for oral (p.o.) administration. Typically, a dosage from about 0.1 mg/kg to about 10 mg/kg may be employed for intramuscular (i.m.) injection. Preferred dosages are in the 1.0 mg/kg to about 100 mg/kg range, and more preferably in the 5 mg/kg to about 50 mg/kg range for i.v. or p.o. administration. The duration of the treatment is usually once per day for a period of three days to three weeks, or until the condition is essentially controlled. Lower doses given less frequently can be used prophylactically to prevent or reduce the incidence of recurrence of the infection.

Aerosol formulations for treatment of the conditions referred to above (e.g., depression) in the average human are preferably arranged such that each metered dose or "puff" of aerosol contains 0.1 micrograms to 100 micrograms of the compound of the invention. The overall daily dose with an aerosol will be within the range of 0.1 mg/kg to about 100 mg/kg, and preferably in the range of 1.0 mg/kg to about 25 mg/kg. Administration may be several times daily, for example 2, 3, 4 or 8 times, giving for example 1, 2 or 3 doses each time.

Examples of the disorders or conditions which may be treated by a compound, composition and method of this invention include: depression, mood disorders, schizophrenia, and addiction.

As an example, the mammal in need of treatment or prevention may be a human. As another example, the mammal in need of treatment or prevention may be a mammal other than a human.

In so far as the compounds of formula I of this invention are basic compounds, they are capable of forming a variety of different salts with various inorganic and organic acids. Although such salts must be pharmaceutically acceptable for administration to animals, including humans, it is often desirable in practice to initially isolate the base compound from the reaction mixture as a pharmaceutically unacceptable salt, then isolate the base by treatment of the salt with an alkaline reagent and finally convert the isolated free base compound to a pharmaceutically acceptable acid addition salt.

The acids which are used to prepare the pharmaceutically acceptable acid salts of the active compound used in formulating the pharmaceutical composition of this invention that are basic in nature are those which form non-toxic acid addition salts, e.g., salts containing pharmacologically acceptable anions. Non-limiting examples of the salts include the acetate, benzoate, beta-hydroxybutyrate, bisulfate, bisulfite, bromide, butyne-1,4-dioate, caproate, chloride, chlorobenzoate, citrate, dihydrogen phosphate, dinitrobenzoate, fumarate, glycollate, heptanoate, hexyne-1,6-dioate, hydroxybenzoate, iodide, lactate, maleate, malonate, mandelate, metaphosphate, methanesulfonate, methoxybenzoate, monohydrogen phosphate, naphthalene-1-sulfonate, naphthalene-2-sulfonate, oxalate, phenylbutyrate, phenylpropionate, phosphate, phthalate, phenylacetate, propanesulfonate, propiolate, propionate, pyrophosphate, pyrosulfate, sebacate, suberate, succinate, sulfate, sulfite, sulfonate, tartrate, xylenesulfonate, trifluoroacetate, acid phosphate, acid citrate, bitartrate, succinate, gluconate, saccharate, nitrate, methanesulfonate, and pamoate {i.e., 1,1'-methylene-bis-(2-hydroxy-3-naphthoate)] salts.

Also included within the scope of this invention are solvates and hydrates of compounds of formula I and their pharmaceutically acceptable salts. The present invention includes within its scope all possible stoichiometric and non-stoichiometric forms.

In the examples that follow, the abbreviations used are intended to have the following, general meaning:
bm: broad multiplet (NMR)
bs: broad singlet (NMR)
d: doublet (NMR)
dd: doublet of doublets (NMR)
d.e.: diatomaceous earth, filtering agent
calcd.: calculated value
equiv: equivalent
J: coupling constant (NMR)
HPLC: high pressure liquid chromatography
LC: liquid chromatography
m: multiplet (NMR)
min: minute(s)
m/z: mass to charge ratio (mass spectroscopy)
obsd: observed value
Rf: retention factor (chromatography)
RT: retention time (chromatography)
rt: room temperature (typically 25° C.)
s: singlet (NMR)
t: triplet (NMR),
T: temperature
tlc: thin layer chromatography
TFA: trifluoroacetic acid
THF: tetrahydrofuran Solvents were purchased and used without purification. Yields were calculated for material judged homogeneous by thin layer chromatography and NMR. Thin layer chromatography was performed on Kieselgel plates eluting with the indicated solvents, visualized by using a 254 nm UV lamp, or stained with an aqueous $KMnO_4$ solution, an ethanolic solution of 12-molybdophosphoric acid.

Nuclear Magnetic Resonance (NMR) spectra were acquired on 90- or 400-MHz NMR Spectrometers. Chemical shifts for proton (i.e., $^1H$) NMR spectra are reported in parts per million (ppm) relative to the singlet of $CDCl_3$ at 7.24 ppm.

Conditions for High Pressure Liquid Chromatography—Mass Spectrometry (HPLC-MS) analysis:
Column: Zorbax RRHD Eclipse Plus (Agilent) $C_{18}$, 1.9 micron, 50 mm×2.1 mm
  Eluent I.
    A: Acetonitrile-$H_2O$=5:95, 20 mM $HCOONH_4$/$NH_4OH$ buffer, pH 7.4
    B: Acetonitrile-$H_2O$=80:20, 20 mM $HCOONH_4$/$NH_4OH$ buffer, pH 7.4

Eluent II.

A: H₂O with 0.1% TFA, pH 2.2

B: Acetonitrile with 0.1% TFA, pH 2.2

Gradient program: adjusted according to the compound properties; typically, start: 0% B to 100% B in 1 minute, 0.8 minute isocratic B.

Column Temp.: 40° C.

Flow Rate: 0.6 mL/min

Sample Conc.: ca. 1 mg/mL

Sample Solvent: Acetonitrile

Injection: 0.5 µL

Detection wavelength: 220 nm

Mass Spectrum (MS) conditions:

Measured Mass Range: 100-750 Daltons

Scan Time: 0.2 s

Ion mode: ES±

Cone Voltage: 20 V

Capillary Voltage: 3 V

Source temp.: 140° C.

Desolvation temp.: 450° C.

Desolvation gas: 450 L/h

Cone gas: 60 L/h

EXAMPLE 1

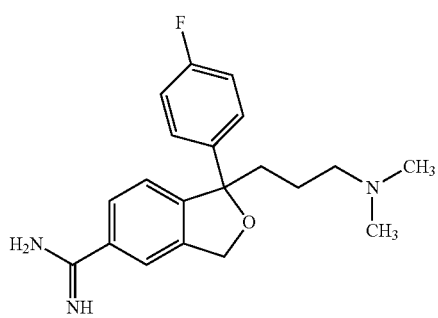 [SMILES: CN(C)CCCC1(c2ccc(F)cc2)OCc2cc(C(=N)N)ccc21]

1-[3-(dimethylamino)propyl]-1-(4-fluorophenyl)-1,3-dihydro-2-benzofuran-5-carboximid-amide A mixture of 1-[3-(dimethylamino)propyl]-1-(4-fluorophenyl)-1,3-dihydro-2-benzofuran-5-carbonitrile hydrobromide (citalopram hydrobromide, 300 mg, 1.0 equiv), copper(II) chloride (1.5 equiv) and ammonia (2.8 equiv) in ethanol (6 mL) was heated at 80° C. for 48 h. The mixture was cooled to room temperature and concentrated to dryness to give crude product (M/Z 342 [M⁺+H]). This material was purified by re-suspending the crude product in fresh ethanol, filtration to remove insoluble material and slow evaporation under N₂ to give the title product, 90 mg (23%) of a pale yellow powder.

LC: 97%;

MS: calcd. for $C_{20}H_{24}FN_3O$: 341.2; obsd. 342 (M⁺+H).

The following compounds 2 through 8 were also prepared using the general procedure as described for the title compound of Example 1.

EXAMPLE 2

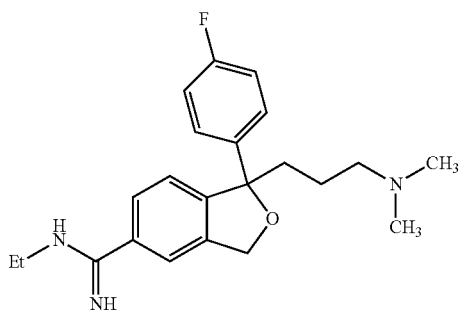 [SMILES: CCNC(=N)c1ccc2c(c1)COC2(CCCN(C)C)c1ccc(F)cc1]

N-ethyl-1-[3-(dimethylamino)propyl]-1-(4-fluorophenyl)-1,3-dihydro-2-benzofuran-5-car-boximidamide Using 250 mg of 1-[3-(dimethylamino)propyl]-1-(4-fluorophenyl)-1,3-dihydro-2-benzofuran-5-carbonitrile hydrobromide (citalopram HBr, 1.0 equiv) and ethylamine (1.3 equiv) gave, after heating at 80° C. for 15 h, the title product (65 mg, 19% yield) as a white solid.

LC: 91%;

MS: calcd. for $C_{22}H_{28}FN_3O$: 369.2; obsd. 370 (M⁺+H).

EXAMPLE 3

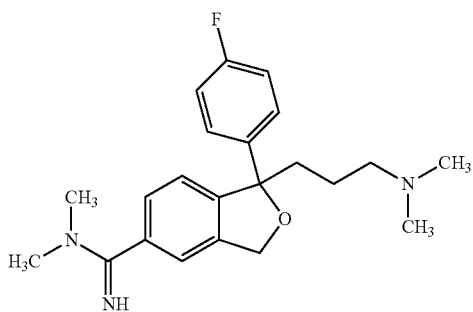

N,N-dimethyl-1-[3-(dimethylamino)propyl]-1-(4-fluorophenyl)-1,3-dihydro-2-benzofuran-5-carboximidamide Using 300 mg of 1-[3-(dimethylamino)propyl]-1-(4-fluorophenyl)-1,3-dihydro-2-benzofuran-5-carbonitrile hydrobromide (citalopram HBr) and dimethylamine (1.3 equiv) gave, after heating at 80° C. for 14 h, title product (90 mg, 26% yield) as a light yellow semisolid.

LC: 99%;

MS: calcd. for $C_{22}H_{28}FN_3O$: 369.2; obsd. 370 (M$^+$+H).

EXAMPLE 4

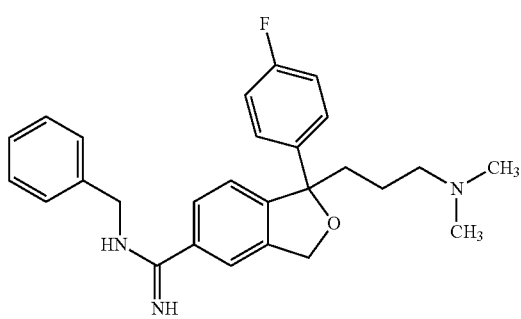 [SMILES: CN(C)CCCC1(c2ccc(F)cc2)OCc2cc(C(=N)NCc3ccccc3)ccc21]

N-benzyl-1-[3-(dimethylamino)propyl]-1-(4-fluorophenyl)-1,3-dihydro-2-benzofuran-5-carboximidamide Using 250 mg of 1-[3-(dimethylamino)propyl]-1-(4-fluorophenyl)-1,3-dihydro-2-benzofuran-5-carbonitrile hydrobromide (citalopram HBr) and benzylamine (1.2 equiv) gave, after heating at 80° C. for 14 h, title product (72 mg, 19% yield) as a white solid.

LC: 97%;

MS: calcd. for $C_{27}H_{30}FN_3O$: 431.2; obsd. 432 (M$^+$+H).

EXAMPLE 5

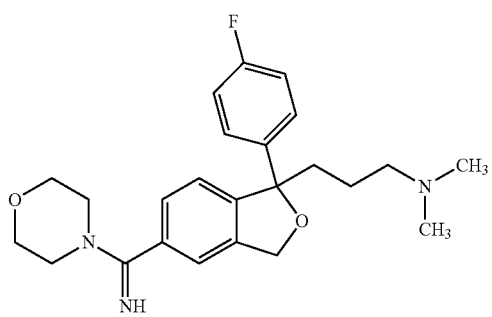 [SMILES: CN(C)CCCC1(c2ccc(F)cc2)OCc2cc(C(=N)N3CCOCC3)ccc21]

1-[1-[3-(dimethylamino)propyl]-1-(4-fluorophenyl)-1,3-dihydro-2-benzofuran-5-yl]-1-(morpholine-4-yl) methanimine Using 400 mg of 1-[3-(dimethylamino)propyl]-1-(4-fluorophenyl)-1,3-dihydro-2-benzofuran-5-carbonitrile hydrobromide (citalopram HBr) and morpholine (1.5 equiv) gave, after heating at 80° C. for 28 h, title product (75 mg, 15% yield) as a white solid.

LC: 96.9%;

MS: calcd. for $C_{24}H_{30}FN_3O_2$: 411.2; obsd. 412 (M$^+$+H).

EXAMPLE 6

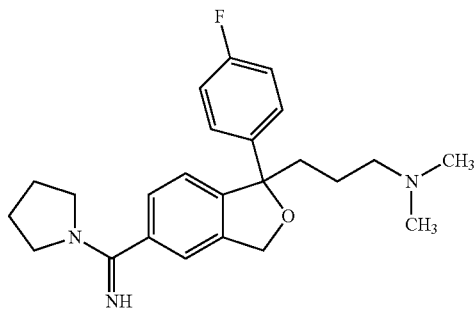 [SMILES: CN(C)CCCC1(c2ccc(F)cc2)OCc2cc(C(=N)N3CCCC3)ccc21]

1-[1-[3-(dimethylamino)propyl]-1-(4-fluorophenyl)-1,3-dihydro-2-benzofuran-5-yl]-1-(pyrrolidin-1-yl) methanimine Using 100 mg of 1-[3-(dimethylamino)propyl]-1-(4-fluorophenyl)-1,3-dihydro-2-benzofuran-5-carbonitrile hydrobromide (citalopram HBr) and pyrrolidine (1.2 equiv) gave, after heating at 80° C. for 14 h, title product (58 mg, 40% yield) as a light yellow solid.

LC: 91%;

MS: calcd. for $C_{24}H_{30}FN_3O.2HCl$: 395.2; obsd. 396 (M$^+$+H).

$^1$H-NMR (DMSO-d$_6$, 400 MHz, T=30° C.) δ 1.52 (m, 2H), 1.85 (m, 2H), 2.05 (m, 2H), 2.20 (m, 2H), 2.35 (m, 2H), 2.65 (s, 6H), 3.05 (m, 2H), 3.38 (m, 2H), 3.53 (m, 2H), 5.22 (q, 2H), 7.18 (m, 2H), 7.60 (m, 4H), 7.75 (d, 1H), 8.80 (s, 1H), 9.22 (s, 1H), 10.15 (bs, 1H).

EXAMPLE 7

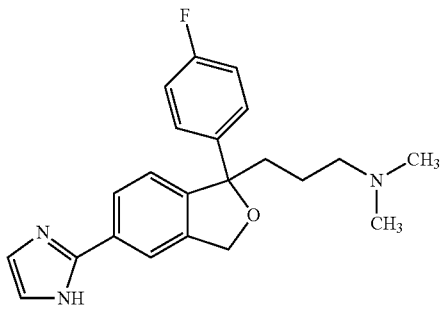 [SMILES: CN(C)CCCC1(c2ccc(F)cc2)OCc2cc(-c3ncc[nH]3)ccc21]

2-(1-[3-(dimethylamino)propyl]-1-(4-fluorophenyl)-1,3-dihydro-2-benzofuran-5-yl])-1H-imidazole 1-[3-(dimethylamino)propyl]-1-(4-fluorophenyl)-1,3-dihydro-2-benzofuran-5-carbo-nitrile hydrobromide (citalopram HBr, 300 mg, 1.0 equiv.) was converted to its free base using saturated aqueous Na$_2$CO$_3$ and EtOAc. The resulting oil was combined with copper(I) chloride (1.5 equiv.) in anhydrous ethanol (6 mL), treated with aminoacetaldehyde diethylacetal (1.3 equiv., Aldrich Chemical Co.) and heated under N$_2$ at 80° C. for 14 hr. Without purification, the mixture containing the intermediate acetal was treated with ethanol (8 mL) and 6N HCl (2 mL) at 80° C. for 2 hr. The reaction mixture was cooled to room temperature, the solvent removed in vacuo and the residue purified by re-suspending the crude product in fresh ethanol, filtration to remove insoluble material and slow evaporation under $N_2$ to produce the title product, 65 mg (12%) as a light yellow solid.

LC: 96.1%;

MS: calcd. for $C_{22}H_{24}FN_3O$: 365.2; obsd. 366 ($M^++H$).

$^1$H-NMR (DMSO-$d_6$, 400 MHz, T=30° C.) δ1.34-1.71 (m, 2H), 2.25 (m, 2H), 2.65 (s, 6H), 3.05 (m, 2H), 5.25 (q, 2H), 7.18 (m, 2H), 7.62 (m, 2H), 7.75 (m, 2H), 7.85 (m, 1H), 8.05 (m, 1H), 8.12 (m, 1H), 10.0 (bs, 1H), 14.9 (bs, 1H).

Opioid Receptor Affinity

The compound of Example 7 was tested for activity vs. opioid receptor subtypes, at an initial concentration of 10 μM, through the NIMH Psychoactive Drug Screening Program (PDSP), operated by Dr. Bryan Roth and his colleagues in the Department of Pharmacology at the University of North Carolina (Chapel Hill, N.C.) through an agreement with the National Institute of Mental Health (NIMH).

DATA

| Opioid Receptor Subtype | Inhibition (%) at 10 μM | Ki (nM) |
|---|---|---|
| Kappa | 100.2 | 47 |
| Mu | 39.1 | n.d. |
| Delta | 23.5 | n.d. | n.d. = not determined

The invention claimed is:

1. A method of treatment of a disorder or condition selected from the group consisting of depression, mood disorders, schizophrenia, anxiety and addiction, the method comprising administering to a mammal in need of such treatment a therapeutically effective amount of a compound of the formula (I):

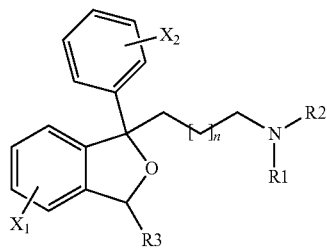

or a pharmaceutically acceptable salt thereof, wherein:

$X_1$ is a group of the general formula (II):

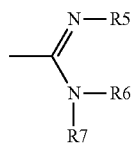

or $X_1$ is a heteroaryl ring, selected from the list comprising 2-imidazolyl, 4-imidazolyl, 2-thiazolyl, 4-thiazolyl, 5-thiazolyl, 2-oxazolyl, 4-oxazolyl, 5-oxazolyl, 1,2,4-thiadiazol-3-yl, 1,2,4-thiadiazol-2-yl, 1,2,4-thiadiazol-4-yl, 1,2,3-triazolyl-2-yl, 1,2,3-triazol-1-yl, 1,2,4-triazol-1-yl, 1,2,4-triazol-3-yl, 1,2,4-triazol-4-yl, 1,3-thiazol-2-yl, 1,3-thiazol-4-yl, 1,2,3,4-tetrazol-5-yl, 1,2,3,4-tetrazol-1-yl, 1,2,4-oxadiazol-3-yl, 1,2,4-oxadiazol-2-yl, 1,2,4-oxadiazol-3-yl, 1,2,4-oxadiazol-5-yl, 1,3-pyrimidin-2-yl, 1,2-pyrazin-3-yl and 1,2,4-triazin-3-yl;

R5, R6 and R7 are independently selected from the list consisting of H, $C_1$-$C_6$ alkyl, $C_3$-$C_7$-cycloalkyl, aryl and heteroaryl; or R5 and R6, taken together with the N—C=N group to which they are attached, form a 5-10 membered cyclic or bicyclic ring, optionally substituted with up to two additional heteroatoms selected from the group consisting of N, O and S; or R6 and R7 taken together with the nitrogen atom to which they are attached form a 5-10 membered cyclic or bicyclic ring, optionally substituted with up to two additional heteroatoms selected from the group consisting of N, O and S, and comprising the rings azetidine, pyrrolidine, piperidine, azepine, piperazine, morpholine and thiomorpholine;

$X_2$ is H, Cl or F;

R1 and R2 are independently hydrogen or methyl;

R3 is hydrogen; and n is zero, one or two.

2. The method of claim 1, wherein R1 and R2 are both hydrogen.

3. The method of claim 1, wherein R3 is hydrogen.

4. The method of claim 1, wherein $X_2$ is 4-fluoro.

5. The method of claim 1, wherein n is one.

6. The method of claim 1, wherein $X_1$ is a heteroaryl ring selected from the list comprising 2-imidazolyl, 4-imidazolyl, 2-thiazolyl, 4-thiazolyl, 5-thiazolyl, 2-oxazolyl, 4-oxazolyl, 5-oxazolyl, 1,2,4-thiadiazol-3-yl, 1,2,4-thiadiazol-2-yl, 1,2,4-thiadiazol-4-yl, 1,2,3-triazolyl-2-yl, 1,2,3-triazol-1-yl, 1,2,4-triazol-1-yl, 1,2,4-triazol-3-yl, 1,2,4-triazol-4-yl, 1,3-thiazol-2-yl, 1,3-thiazol-4-yl, 1,2,3,4-tetrazol-5-yl, 1,2,3,4-tetrazol-1-yl, 1,2,4-oxadiazol-3-yl, 1,2,4-oxadiazol-2-yl, 1,2,4-oxadiazol-3-yl, 1,2,4-oxadiazol-5-yl, 1,3-pyrimidin-2-yl, 1,2-pyrazin-3-yl and 1,2,4-triazin-3-yl.

7. The method of claim 1, wherein $X_1$ is a group of the general formula (II):

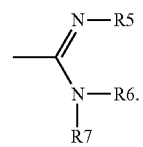

8. The method of claim 1, wherein R5 and R6, taken together with the N—C=N group to which they are attached form a 4-7 membered cyclic or bicyclic ring, optionally substituted with up to two additional heteroatoms selected from the group consisting of N, O and S.

9. The method of claim 1, wherein R6 and R7, taken together with the nitrogen atom to which they are attached form a 4-7 membered cyclic or bicyclic ring, optionally substituted with up to two additional heteroatoms selected from the group consisting of N, O and S, and comprising the rings azetidine, pyrrolidine, piperidine, azepine, piperazine, morpholine, thiomorpholine, oxazole and thiazole.

10. The method of claim 1, wherein R1 is hydrogen, R2 is hydrogen, R3 is hydrogen, n is one, $X_2$ is 4-fluoro.

11. The method of claim 1, wherein the compound is:
- 2-(1-[3-(dimethylamino)propyl]-1-(4-fluorophenyl)-1,3-dihydro-2-benzofuran-5-yl])-1H-imidazole.

12. The method of claim 1, wherein the compound is selected from the group consisting of:
- 2-(1-[3-aminopropyl]-1-(4-fluorophenyl)-1,3-dihydro-2-benzofuran-5-yl])-1H-imidazole;
- 2-(1-[3-(methylamino)propyl]-1-(4-fluorophenyl)-1,3-dihydro-2-benzofuran-5-yl])-1H-imidazole;
- 2-(1-[3-(dimethylamino)propyl]-1-(4-fluorophenyl)-1,3-dihydro-2-benzofuran-5-yl])-1,3-thiazole;
- 2-(1-[3-(dimethylamino)propyl]-1-(4-fluorophenyl)-1,3-dihydro-2-benzofuran-5-yl])-1,3-oxazole;
- 4-(1-[3-(dimethylamino)propyl]-1-(4-fluorophenyl)-1,3-dihydro-2-benzofuran-5-yl])-1,3-thiazole;
- 2-(1-[3-(dimethylamino)propyl]-1-(4-fluorophenyl)-1,3-dihydro-2-benzofuran-5-yl])-1,3-thiazole;
- 3-(1-[3-dimethylamino)propyl]-1-(4-fluorophenyl)-1,3-dihydro-2-benzofuran-5-yl])-1,2-isothiazole;
- 4-(1-[3-(dimethylamino)propyl]-1-(4-fluorophenyl)-1,3-dihydro-2-benzofuran-5-yl])-2-methyl-1H-imidazole;
- 5-(1-[3-(dimethylamino)propyl]-1-(4-fluorophenyl)-1,3-dihydro-2-benzofuran-5-yl])-2,4-dimethyl-1H-imidazole;
- 2-(1-[3-(dimethylamino)propyl]-1-(4-fluorophenyl)-1,3-dihydro-2-benzofuran-5-yl])-1H-1,3,4-triazole;
- 2-(1-[3-(dimethylamino)ethyl]-1-(4-fluorophenyl)-1,3-dihydro-2-benzofuran-5-yl])-1H-imidazole;
- 2-(1-[3-(dimethylamino)butyl]-1-(4-fluorophenyl)-1,3-dihydro-2-benzofuran-5-yl])-1H-imidazole;
- 2-(1-[3-(dimethylamino)propyl]-1-(4-fluorophenyl)-1,3-dihydro-2-benzofuran-5-yl])-4-methyl-1H-imidazole;
- 5-(1-[3-(dimethylamino)propyl]-1-(4-fluorophenyl)-1,3-dihydro-2-benzofuran-5-yl])-1H-tetrazole;
- 1-(1-[3-(dimethylamino)propyl]-1-(4-fluorophenyl)-1,3-dihydro-2-benzofuran-5-yl])-5-methyl-2H-tetrazole;
- 3-(1-[3-(dimethylamino)propyl]-1-(4-fluorophenyl)-1,3-dihydro-2-benzofuran-5-yl])-1,2,4-thiadiazole;
- 3-(1-[3-(dimethylamino)propyl]-1-(4-fluorophenyl)-1,3-dihydro-2-benzofuran-5-yl])-1,2,4-oxadiazole;
- 1-methyl-2-(1-[3-(dimethylamino)propyl]-1-(4-fluorophenyl)-1,3-dihydro-2-benzofuran-5-yl])-1H-imidazole;
- 4-methyl-2-(1-[3-(dimethylamino)propyl]-1-(4-fluorophenyl)-1,3-dihydro-2-benzofuran-5-yl])-1H-imidazole;
- 2(S)-2-(1-[3-(dimethylamino)propyl]-1-(4-fluorophenyl)-1,3-dihydro-2-benzofuran-5-yl])-1H-imidazole;
- 2(R)-2-(1-[3-(dimethylamino)propyl]-1-(4-fluorophenyl)-1,3-dihydro-2-benzofuran-5-yl])-1H-imidazole;
- 2-(1-[3-(dimethylamino)propyl]-1-(4-fluorophenyl)-1,3-dihydro-2-benzofuran-5-yl])-1H-benzimidazole;
- 4,5-dimethyl-2-(1-[3-(dimethylamino)propyl]-1-(4-fluorophenyl)-1,3-dihydro-2-benzofuran-5-yl])-1H-imidazole;
- 2-[1-[3-(dimethylamino)propyl]-1-(4-fluorophenyl)-1,3-dihydro-2-benzofuran-5-yl]-1,2,3,4-tetrahydro-1H-isoquinolin-2-yl)methanimine;
- 2-(1-[3-dimethylaminopropyl]-1-(4-fluorophenyl)-1,3-dihydro-2-benzofuran-5-yl})-1,3-pyrimidine;
- 3-(1-[3-dimethylaminopropyl]-1-(4-fluorophenyl)-1,3-dihydro-2-benzofuran-5-yl})-1,2,4-triazine;
- 2-(1-[3-(dimethylamino)propyl]-1-(4-fluorophenyl)-1,3-dihydro-2-benzofuran-5-yl)-1H-4,5-dihydro-imidazole;
- 2-(1-[3-(dimethylamino)propyl]-1-(4-fluorophenyl)-1,3-dihydro-2-benzofuran-5-yl)-4,5,6,7-tetrahydro-1H-1,3-diazepine; and
- 2-(1-[3-(dimethylamino)propyl]-1-(4-fluorophenyl)-1,3-dihydro-2-benzofuran-5-yl)-1,4,5,6-tetrahydro-pyrimidine.

* * * * *